United States Patent [19]

Stevens et al.

[11] Patent Number: 5,011,020
[45] Date of Patent: Apr. 30, 1991

[54] CYTOTOXIC AGENT CONTAINMENT KIT

[75] Inventors: Kathleen R. Stevens, Sugar Land; Thomas H. Connor, Dickinson, both of Tex.

[73] Assignee: The Board of Regents, The University of Texas System, Austin, Tex.

[21] Appl. No.: 382,434

[22] Filed: Jul. 19, 1989

[51] Int. Cl.⁵ ............................................. A61B 19/02
[52] U.S. Cl. .................................. 206/570; 206/438; 206/803; 206/811
[58] Field of Search ............... 206/438, 223, 803, 811, 206/828, 570, 571, 572, 581, 538, 363, 364, 365, 528; 220/23.83

[56] References Cited

U.S. PATENT DOCUMENTS

| | | | |
|---|---|---|---|
| 1,116,310 | 11/1914 | Maser | 206/572 |
| 2,672,232 | 3/1954 | Kessell, Jr. | 220/521 X |
| 4,520,926 | 6/1985 | Nelson | 206/366 |
| 4,523,679 | 6/1985 | Paikoff et al. | 206/570 |
| 4,595,102 | 6/1986 | Cianci et al. | 206/572 |
| 4,768,651 | 9/1988 | Lanius | 206/373 |

FOREIGN PATENT DOCUMENTS 3038924  5/1982  Fed. Rep. of Germany ...... 206/223

Primary Examiner—Paul T. Sewell
Assistant Examiner—Jacob K. Ackun, Jr.
Attorney, Agent, or Firm—Arnold, White & Durkee

[57] ABSTRACT

A cytotoxic agent containment kit is disclosed which has a top enclosure member and bottom enclosure member that are hingedly connected much like a brief case. The bottom enclosure member has a sealable, nonpermeable container for drugs and another for holding waste such as empty drug containers and used hypodermic needles. A removable tray is provided which acts as a work surface for preparing the drugs for administration. The contents of the kit including the tray and containers can be disposed of after use, and the outer case reused. The kit's nonpermeable construction helps insure that persons handling it will not be accidentally exposed to the cytotoxic agents that it contains.

8 Claims, 3 Drawing Sheets

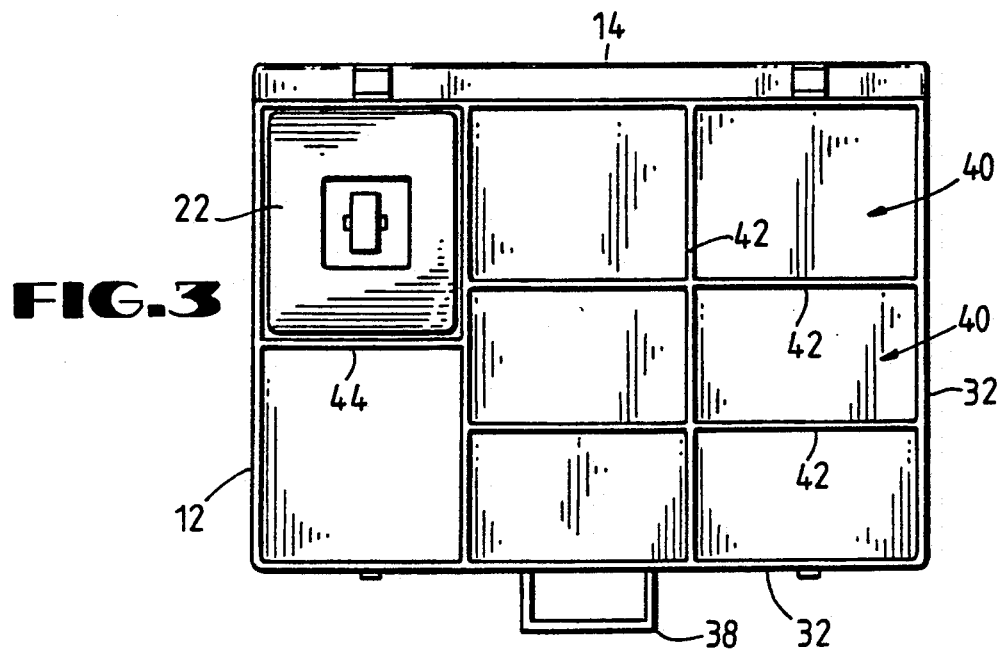
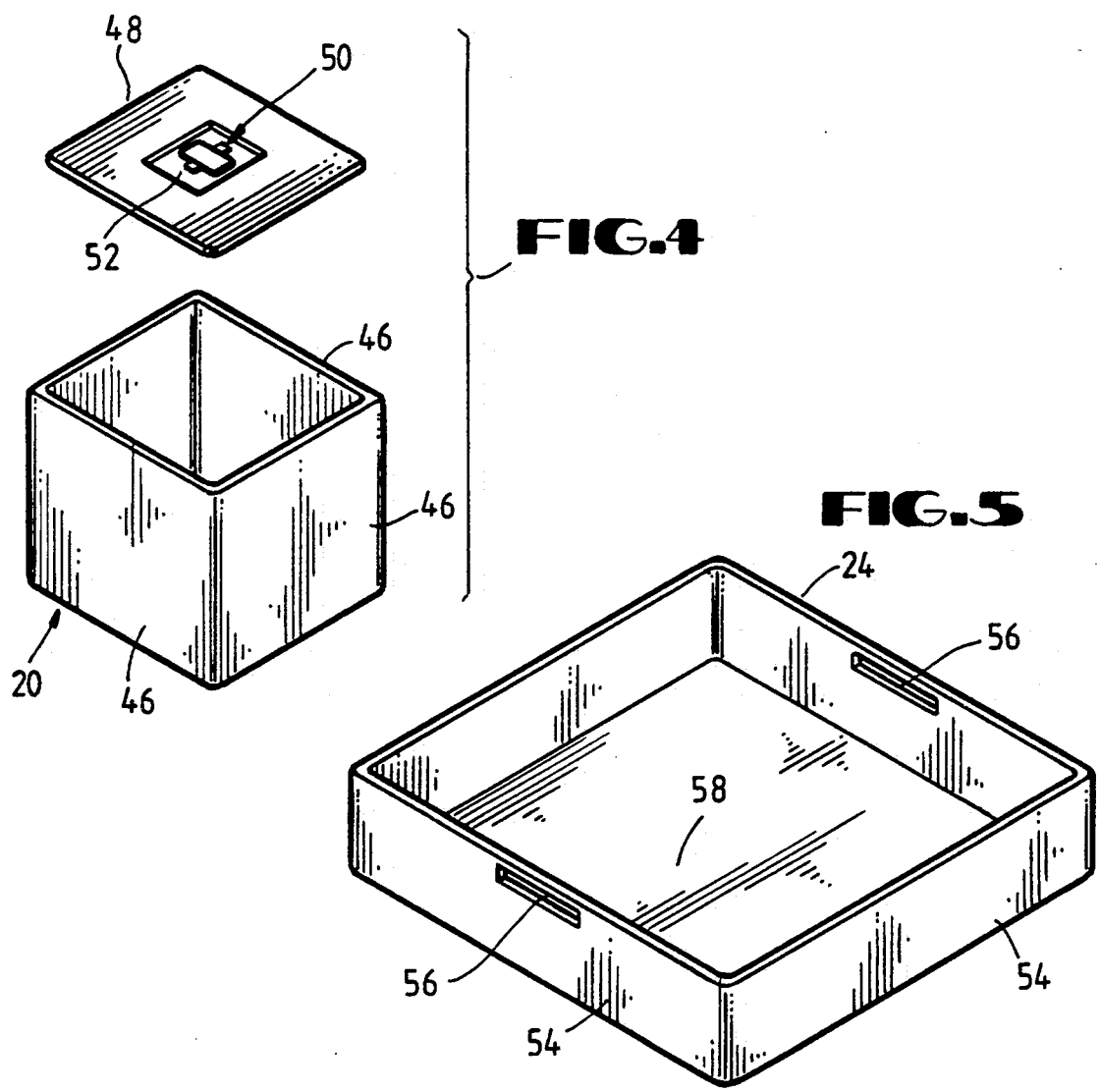

CYTOTOXIC AGENT CONTAINMENT KIT

BACKGROUND OF THE INVENTION

This invention relates to apparatus for use in transporting, storing, administering, and disposing of drugs in a home setting. More specifically, it relates to a preparation and containment kit for cytotoxic drugs.

There is a major trend in the health care industry toward performing technical procedures outside major hospitals, partly in order to reduce costs In addition, the number of newly diagnosed cancer cases is increasing each year. These two factors have resulted in shifting significant amounts of cancer chemotheraphy from major hospitals to home settings, clinics, etc.

The increasing use of home chemotherapy has a number of benefits, but it also has some risks. One risk stems from the highly toxic nature of commonly used antineoplastic drugs. In a hospital setting, these drugs are stored, prepared, and administered very carefully by trained professionals so as to minimize the risk of accidental exposure of those who handle the drugs and the apparatus used to prepare and administer them. In a hospital, safety equipment such as biosafety cabinets, individual refrigeration units, hazardous waste disposal facilities, and dedicated work areas help minimize the risk of accidental exposure. However, in a home setting, much of this safety equipment will not be available. Accordingly, unless appropriate measures are taken, home chemotherapy patients, nurses aiding in their treatment, and family members will be at risk of accidental exposure to cytotoxic agents.

Accordingly, a very important need exists for apparatus that will facilitate the safe storage, preparation, use, and disposal of cytotoxic drugs and related equipment such as needles in a home setting.

SUMMARY OF THE INVENTION

The present invention relates to a disposable containment kit for drugs and related equipment. The kit includes a bottom enclosure member, and a top enclosure member which is hingedly connected at one edge to the bottom enclosure member, whereby the top enclosure and bottom enclosure member can be closed to define a sealed enclosure. The kit also includes a sealable, substantially leakproof, nonpermeable drug container which is adapted to hold drugs and apparatus needed to administer the drugs, and a similar sealable, nonpermeable waste container which is adapted to hold used drug containers and apparatus. In addition, the kit includes at least one storage compartment which is located in the bottom enclosure member, and a removable tray which is adapted to rest on top of the storage compartment. The tray can provide an aseptic, horizontal work surface on which to prepare drugs for administration. This kit can be provided with a handle for carrying. In addition, it will usually include at least one absorbent pad on the removable tray, so that any materials which are spilled can be absorbed, thereby minimizing the risk of human contact with the toxic agents.

The entire kit is a lightweight, partially-disposable unit similar in size to a small brief case. The required drugs would typically be in bags or bottles which are located in the drug container. Protective gloves, hypodermic needles, intravenous connecting tubes, infusion pumps, and other necessary apparatus could be located either in the drug container or in a storage compartment.

When the patient is ready to use the kit, he can unlatch the kit, and remove the drugs and apparatus needed to administer them. The removable tray provides a clean, dedicated work surface on which to prepare the drugs and apparatus. After the drugs have been administered, empty drug containers, used needles, and other contaminated apparatus can be placed in the waste container, which is then sealed. The entire kit is then closed, and can be delivered to an appropriate hospital or waste disposal facility.

The kit of the present invention can be designed either for a single use or for multiple uses. In either event, the contents of the kit along with the tray and containers are disposed of when the patient is done with it.

One specific embodiment of the present invention includes a rectangular, nonpermeable bottom enclosure member which has a rectangular base and four rectangular side walls, the base being divided into a first zone and a second zone, with the two zones being divided by a vertical wall. This embodiment also includes a rectangular, nonpermeable top enclosure member which has a rectangular lid and four rectangular side walls, one edge of one side wall being hingedly connected to a corresponding side wall of the bottom enclosure member. The kit also has a releasable latch to hold the bottom enclosure member and top enclosure member together in a closed position. A sealable, nonpermeable drug container in the form of a rectangular box with an open top is also included. This container rests in the first zone of the bottom enclosure member, and also has a latchable top lid and a latch to secure the top lid in the closed position. This container could be insulated for drugs that require cold storage during transportation. Likewise, there is a sealable, nonpermeable waste container which is also in the form of a rectangular box with an open top, this container also resting in the first zone of the bottom enclosure member and having a latchable top lid with a latch to secure the top lid in the closed position. A plurality of storage compartments are located in the second zone of the bottom enclosure member, these storage compartments being defined by side walls of the bottom enclosure member and at least one internal vertical wall, the storage compartments further being open at their tops. Finally, a removable horizontal tray rests on top of the storage compartments and covers the second zone of the bottom enclosure member.

The present invention has a number of benefits. It facilitates the use of parenteral drugs, especially cytotoxic aqents, outside of major treatment facilities. It provides a convenient, clean, portable work area for the preparation of chemotherapy and a safe means of storage and disposal of drugs and waste material resulting from their use. The present invention reduces the possibility of inadvertent exposure to hazardous cytotoxic agents by patients' families and health care personnel. It also provides a safe method for disposal of needles which will reduce inadvertent needle sticks.

BRIEF DESCRIPTION OF THE DRAWINGS

FIG. 3 is a top view of the kit in the open position with the tray removed.

FIG. 4 is a perspective view of a drug container with its top removed.

FIG. 5 is a perspective view of a removable tray.

DETAILED DESCRIPTION OF A SPECIFIC EMBODIMENT

Figure 1:
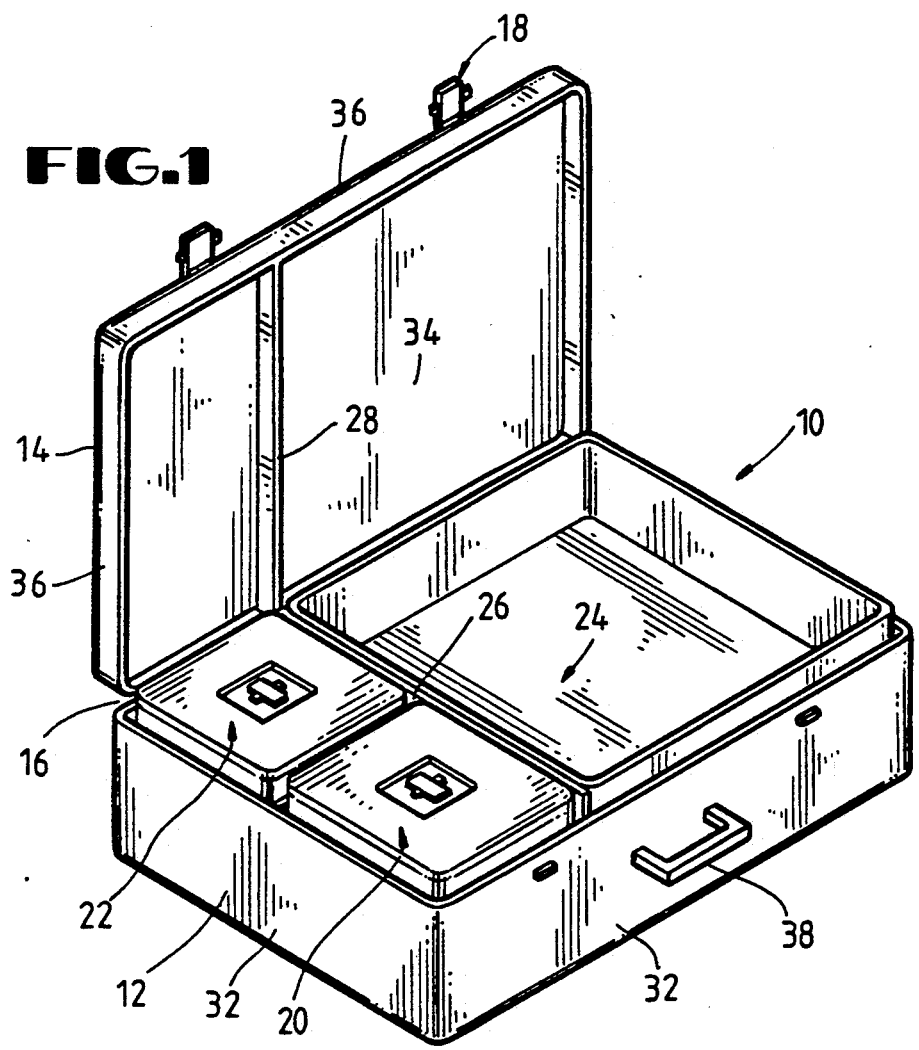
FIG. 1 is a perspective view of a cytotoxic agent containment kit in accordance with the present invention.

A cytotoxic agent containment kit 10 is similar in shape to a brief case. The kit 10 includes a bottom enclosure member 12 and a top enclosure member 14. The two enclosure members 12 and 14 are connected by a hinge 16 running along one edge of each enclosure. One or more outer latches 18 can be provided to secure the bottom enclosure member and top enclosure member together when the kit is in the closed position. (FIG. 1 shows a version having one latch, while FIGS. 2A–C and 3 show a version with two latches.) When the kit is closed, it provides a tight seal to prevent leakage of any spilled drugs.

When the kit is open as shown in FIG. 1, one sees the top of a drug container 20, a waste container 22, and a removable tray 24. A narrow divider wall 26 runs from one side of the bottom enclosure member 12 to the other, thereby separating the removable tray 24 from the drug container 20 and waste container 22. A corresponding divider wall 28 is located in the top enclosure member 14. When the kit is closed, the divider wall 26 in the bottom enclosure member 12 and the divider wall 28 in the top enclosure member 14 are aligned one on top of the other.

Both the bottom enclosure member 12 and the top enclosure member 14 are rectangular in shape, although they can have rounded corners and edges. The former has a rectangular bottom 30 and four side walls 32. The top enclosure member 14 likewise has a rectangular lid 34 and four rectangular side walls 36. A handle 38 is provided on one side wall 32 of the bottom enclosure 12 for ease of carrying.

Figure 2A:
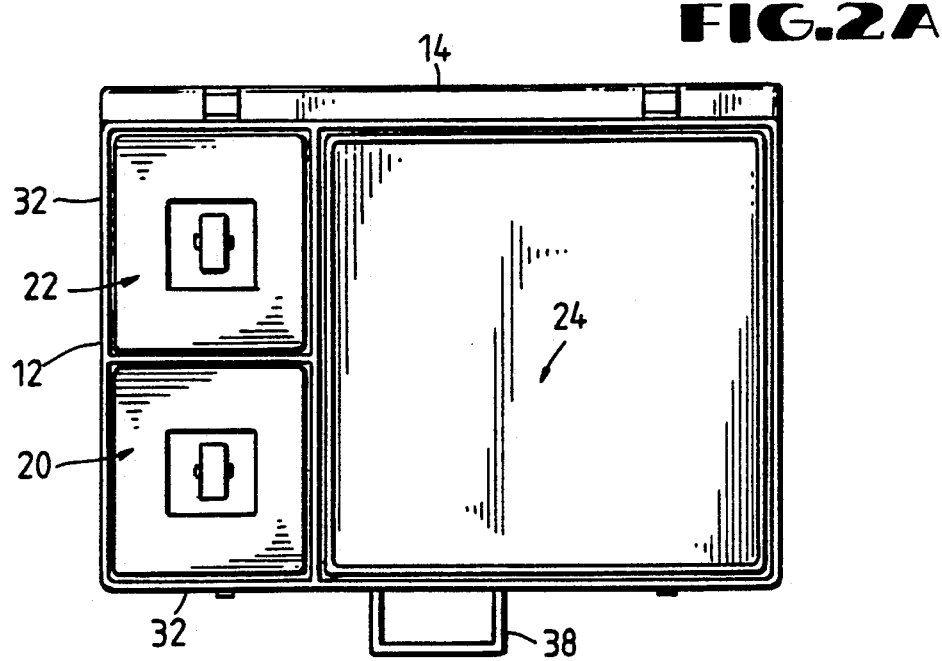
FIGS. 2A, 2B, and 2C are top, front, and side views, respectively, of the kit in an open position.
Figure 2C:
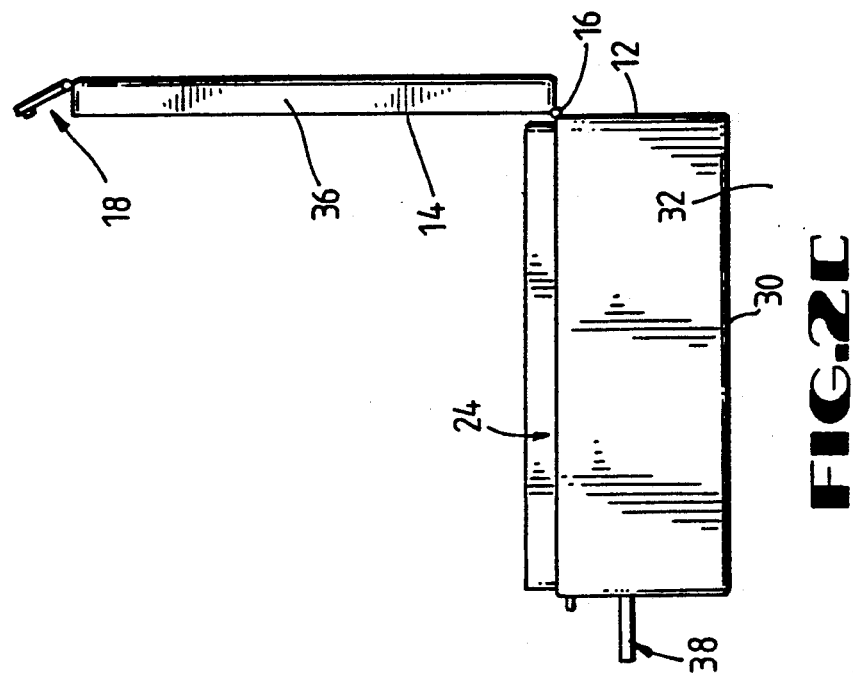
Figure 2B:
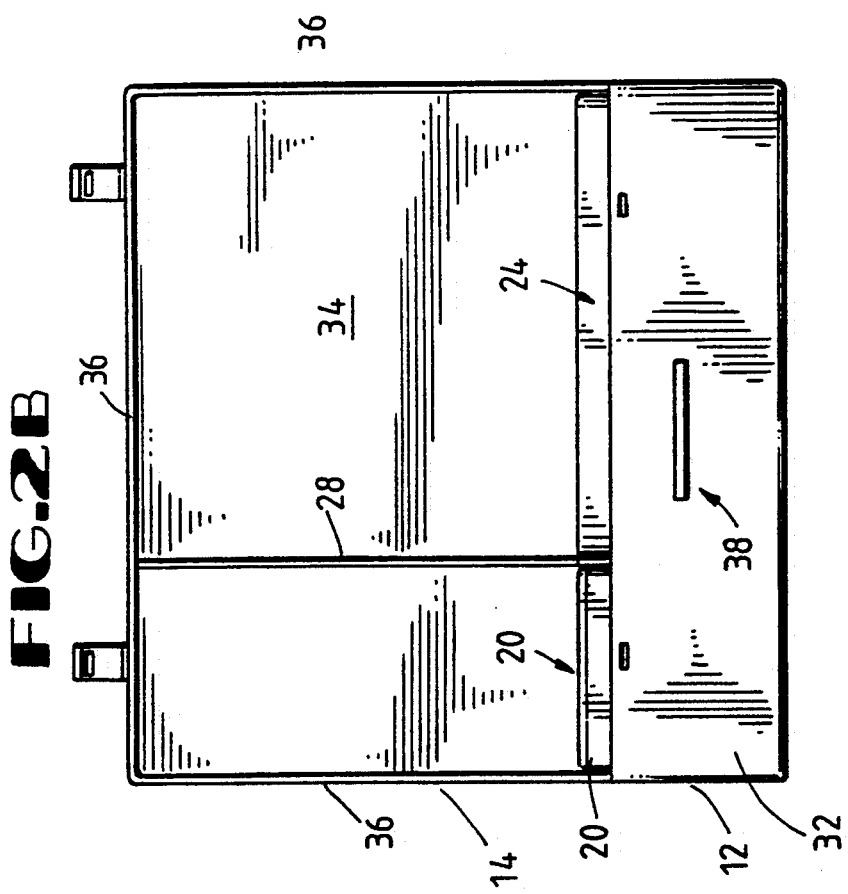

As can be seen in FIGS. 1, 2B and 2C, the drug container 20, waste container 22, and the upper edges of the removable tray 24 extend slightly above the top of the bottom enclosure member 12. When the upper enclosure member 14 is swung down into the closed position, the flat lid 34 of the top enclosure member 14 should be in very close proximity to the upper edges of the removable tray 24, and the drug and waste containers 20 and 22. This will prevent the two containers 20 and 22 and the tray 24 from shifting while the kit is being transported, by allowing no room for those items to move within the enclosure.

The divider wall 26 in the bottom enclosure member 12 divides it into two zones. The first zone comprises the spaces for receiving the drug container 20 and the waste container 22. The second zone comprises the space in which the removable tray 24 rests. The first zone is fully filled by the drug container 20 and waste container 22, and therefore they cannot shift back and forth when the kit is transported. Likewise, the entire area of the second zone is covered by the removable tray 24 so that it too will not shift during transportation.

Turning now to FIG. 3, when the removable tray 24 is removed, a plurality of storage compartments 40 can be seen. These storage compartments 40 are defined by some of the side walls 32 of the bottom enclosure member 12, along with a plurality of internal divider walls 42. If desired, another divider wall 44 can be used to separate the space for the drug container 20 from that for the waste container 22.

The drug container 20, which is shown as being removed in FIG. 3, can be seen in more detail in FIG. 4. It includes a box having a flat bottom and four side walls 46 and a removable top lid 48. The inner surface of the bottom and side walls can be thermally insulated if desired. A latch 50 is used to hold the lid 48 in place when the lid is in the closed position, and to release the lid when access is needed to the contents of the container 20. The latch 50 is preferably located in a small recess 52.

The waste container 22 would have the same construction. Preferably within the waste container 22 is a specific area to accommodate used needles. This area will protect the user from accidental used needle sticks by isolating the used needles from further touch. This can be accomplished either by a one-way entrapment door or by a dartboard type material into which the needle is stuck upon disposal.

Although FIG. 4 shows the lid 48 as being completely removable from the container 20, it would also be possible for the lid and container to be hingedly connected at one edge.

The removable tray 24 is shown in more detail in FIG. 5. The tray 24 has a flat bottom and four side walls 54. If desired, small apertures 56 can be made in opposing side walls 54 so as to provide hand holds for moving the tray 24. Inside the tray 24, it is preferred to have a plurality of absorbent pads 58 to soak up any liquids that are spilled. One example of a suitable pad material is the Chemo Safety Prep mat available from Chemo Safety Systems, San Diego, Calif. The pads 58 are preferably removable, and located one on top of another, so that a contaminated pad can be removed and placed in the waste container 22, leaving a clean pad remaining on the tray 24. It is also possible to treat the pad with a chemical reagent that will change color when contacted by a preselected cytotoxic agent. This will provide the user with a warning when a quantity of the cytotoxic agent has been spilled on the pad, so that the user will know of the need to avoid that spill and to dispose of the absorbent pad 58.

In another embodiment, clean pads could be stored in a storage compartment 40, and removed as needed to be placed on the tray 24.

Although the tray is shown in the drawings as not covering the drug container 20 or the waste container 22, another embodiment of the invention could have a tray that covered them as well.

The kit 10 would normally be provided to a patient with a supply of the required chemotherapy drugs in appropriate bags or bottles, infusion pumps, etc. placed in the drug container 20. The kit would likely also contain apparatus such as infusion pumps, hypodermic needles, tubing, protective gloves, and other things that would be needed to prepare and administer the drugs. These items could be placed in the drug container 20, or in any of the storage compartments 40. When the patient or nurse is ready to administer the drugs, the drugs and other apparatus are withdrawn from the drug container 20 and the storage compartments 40, and are placed on top of the tray 24. With the tray 24 removed from the top of the storage compartments 40, it provides an aseptic work surface for the necessary operations to prepare the drugs for administration.

After administration of the drugs is complete, empty drug bags or bottles, used needles, used gloves, and other contaminated materials can be placed in the waste container 22, and once the top lid of the waste container is in place, the contaminated materials are then effectively sealed within a leakproof, nonpermeable container, thereby minimizing the risk of exposure to the contents thereof. The waste container 22 preferably includes a repository for used needles.

It is possible to design a kit in accordance with the present invention for multiple uses, or for a single use. In either case, once the desired number of uses are complete, the tray and containers can be disposed of in an appropriate waste disposal facility. The outer case is preferably constructed of a more durable plastic and may be cleaned and reused. This eliminates the need to dispose of the individual items separately, and thereby significantly reduces the required handling and associated risk of inadvertent exposure to cytotoxic agents.

The tray and containers of a kit in accordance with the present invention are preferably constructed of a light, durable material, which is inexpensive enough to make it practical to discard them. Further, it is preferred that the entire kit be capable of being placed in a refrigerator. A variety of plastics would be satisfactory for this purpose.

Although the present invention has been described in terms of chemotherapy drugs, it could also be used with antibiotics, nutritional supplements, or the like. When it is used with cytotoxic agents, it will usually have a label on its exterior and on the drug and waste containers to identify them as containing hazardous material.

The preceding description is intended to illustrate one embodiment of the present invention. It is not intended to be an exhaustive description of all possible embodiments of the present invention. Those skilled in this field will recognize that a number of modifications could be made to this embodiment which would still remain within the scope of the present invention.

We claim:

1. A disposable containment kit for drugs, including:
 a bottom enclosure member;
 a top enclosure member which is hingedly connected at one edge to the bottom enclosure, whereby the top enclosure and bottom enclosure can be closed to define a sealed enclosure;
 a sealable, substantially leakproof drug container which is impermeable to liquid and located within the enclosure defined by the top enclosure member and the bottom enclosure member and is capable of holding drugs and apparatus needed to administer the drugs;
 a sealable waste container which is impermeable to liquid and located within the enclosure defined by the top enclosure member and the bottom enclosure member and is capable of holding used drug containers and apparatus;
 at least one storage compartment which is located in the bottom enclosure;
 a removable tray which is adapted to rest on top of the storage compartment, and which can be removed to provide an aseptic work surface on which to prepare drugs for administration; and
 at least one absorbent pad on the removable tray; which absorbent pad covers the upper surface of the tray and is removable from the tray, and which absorbent pad contains a chemical reagent which changes in color when a selected drug contacts it.

2. A cytotoxic agent containment kit, including:
 a rectangular bottom enclosure member which is impermeable to liquid and has spaces for a drug container and a waste container, and at least one storage compartment which is located beside the drug container and waste container;
 a rectangular top enclosure member which is impermeable to liquid and hingedly connected at one edge to the bottom enclosure, whereby the top enclosure and bottom enclosure can be closed to define a sealed enclosure;
 a releasable latch to hold the bottom enclosure and top enclosure in a mutually sealed position;
 a sealable drug container which is impermeable to liquid and comprises a rectangular box with an open top, a top lid which can be closed to seal the container, and a latch to secure the top lid in the closed position;
 a sealable waste container which is impermeable to liquid and comprises a rectangular box with an open top, a top lid which can be closed to seal the container, and a latch to secure the top lid in the closed position;
 at least one storage compartment which is located in the bottom enclosure;
 a rectangular, removable, horizontal tray which is adapted to rest on top of the storage compartment in the bottom enclosure, and provides an aseptic, horizontal work surface on which to prepare drugs for administration; and
 at least one absorbent pad on the removable tray which absorbent pad covers the upper surface of the tray and is removable from the tray, and which absorbent pad contains a chemical reagent which changes in color when a selected drug contacts it.

3. A cytotoxic agent containment kit, including:
 a rectangular, nonpermeable bottom enclosure member which has a rectangular base and four rectangular side walls, the base being divided into a first zone and a second zone, with the two zones being divided by a vertical wall;
 a rectangular, nonpermeable top enclosure member which has a rectangular lid and four rectangular side walls, one edge of one side wall being hingedly connected to a corresponding side wall of the bottom enclosure;
 a releasable latch to hold the bottom enclosure and top enclosure together in a closed position;
 a sealable, nonpermeable drug container in the form of a rectangular box with an open top, the container resting in the first zone of the bottom enclosure, the container further having a latchable top lid and a latch to secure the top lid in the closed position;
 a sealable, nonpermeable waste container in the form of a rectangular box with an open top, the container resting in the first zone of the bottom enclosure, the container further having a latchable top lid and a latch to secure the top lid in the closed position, and the container including a repository for used needles;
 a plurality of storage compartments in the second zone of the bottom enclosure, the storage compartments being defined by side walls of the bottom enclosure and at least one internal vertical wall, the storage compartments being open at their tops; and
 a removable, horizontal tray which rests on top of the storage compartments and covers the second zone of the bottom enclosure, and which provides an aseptic, horizontal work surface on which to prepare drugs for administration.

4. The kit of claim 3, further including a handle for carrying the kit.

5. The kit of claim 3, where the drug container is thermally insulated.

6. The kit of claim 3, further comprising a plurality of absorbent pads on the removable tray.

7. The kit of claim 6, where the absorbent pads are individually removable from the tray.

8. The kit of claim 6, where each absorbent pad contains a chemical reagent which changes in color when a selected drug contacts it.

* * * * *